(12) United States Patent
Borsari

(10) Patent No.: US 7,677,245 B2
(45) Date of Patent: Mar. 16, 2010

(54) HELMET FOR ARTIFICIAL RESPIRATION

(75) Inventor: Maurizio Borsari, Mirandola-Modena (IT)

(73) Assignee: Dimar S.R.L., Mirandola (IT)

( * ) Notice: Subject to any disclaimer, the term of this patent is extended or adjusted under 35 U.S.C. 154(b) by 218 days.

(21) Appl. No.: 10/513,779

(22) PCT Filed: May 14, 2003

(86) PCT No.: PCT/EP03/05135

§ 371 (c)(1), (2), (4) Date: May 18, 2005

(87) PCT Pub. No.: WO03/097145

PCT Pub. Date: Nov. 27, 2003

(65) Prior Publication Data

US 2005/0199235 A1    Sep. 15, 2005

(30) Foreign Application Priority Data

May 15, 2002  (IT) .................. MI2002A1036
Oct. 8, 2002  (IT) .................. MI20020460 U

(51) Int. Cl.
*A62B 17/00* (2006.01)

(52) U.S. Cl. ................................. 128/201.29

(58) Field of Classification Search ............ 128/201.23, 128/200.24, 201.22, 201.25, 201.28, 201.29, 128/206.21, 206.23, 206.24, 206.28, 207.11; 2/2.15, 171.3, 205, 202, 2.17, 5, 6.1, 6.2, 2/6.6, 421, 422, 2.14, 422.1; 604/43, 173

See application file for complete search history.

(56) References Cited

U.S. PATENT DOCUMENTS

| | | | | | |
|---|---|---|---|---|---|
| 787,167 | A | * | 4/1905 | Gates .................... | 128/206.16 |
| 1,766,300 | A | * | 6/1930 | Washington ........... | 128/201.23 |
| 2,238,759 | A | * | 4/1941 | Hans Vestrem ........ | 128/201.25 |
| 2,742,900 | A | | 4/1956 | Giorgio et al. | |
| 2,910,063 | A | * | 10/1959 | Monroe et. al. ........ | 128/205.24 |
| 2,942,072 | A | * | 6/1960 | Cunningham ............... | 379/430 |
| 2,988,749 | A | * | 6/1961 | Jean-Philippe .................. | 2/205 |
| 2,989,049 | A | * | 6/1961 | Jean-Philippe .............. | 126/208 |
| 3,127,616 | A | * | 4/1964 | Schueller ......................... | 2/6.5 |
| 3,481,333 | A | * | 12/1969 | Garrison ................ | 128/201.28 |
| 3,505,677 | A | * | 4/1970 | Pravaz et. al. .................. | 2/410 |
| 3,895,625 | A | * | 7/1975 | Delest .................... | 128/201.25 |
| 4,186,735 | A | * | 2/1980 | Henneman et al. ..... | 128/201.25 |
| 4,236,514 | A | * | 12/1980 | Moretti .................... | 128/201.23 |
| 4,291,417 | A | * | 9/1981 | Pagano ........................... | 2/202 |
| 4,390,017 | A | * | 6/1983 | Harrison et al. ............. | 604/270 |
| 4,411,264 | A | * | 10/1983 | Jacobson ............... | 128/201.23 |
| 4,458,680 | A | * | 7/1984 | Childers et al. ........ | 128/201.29 |
| 4,534,344 | A | * | 8/1985 | Constance-Hughes . | 128/201.15 |
| 4,552,140 | A | * | 11/1985 | Cowley et al. ......... | 128/201.25 |
| 4,620,538 | A | * | 11/1986 | Koegel et al. .......... | 128/201.23 |
| 4,683,880 | A | * | 8/1987 | Werjefelt ............... | 128/201.28 |
| 4,807,614 | A | * | 2/1989 | van der Smissen et al. ...................... | 128/201.23 |
| 4,949,714 | A | * | 8/1990 | Orr ........................ | 128/200.24 |
| 5,003,974 | A | * | 4/1991 | Mou ...................... | 128/201.25 |
| 5,059,170 | A | * | 10/1991 | Cameron ...................... | 604/43 |
| 5,226,409 | A | * | 7/1993 | Bower et al. ............ | 128/201.23 |
| 5,272,770 | A | * | 12/1993 | Allen et al. ..................... | 2/421 |
| 5,443,452 | A | * | 8/1995 | Hart et al. .............. | 604/167.03 |
| 5,477,566 | A | * | 12/1995 | Massman ........................ | 2/424 |
| 5,549,104 | A | * | 8/1996 | Crump et al. .......... | 128/201.25 |
| 5,569,182 | A | * | 10/1996 | Twardowski et al. .......... | 604/43 |
| 5,676,133 | A | | 10/1997 | Hickle et al. | |
| 5,819,728 | A | * | 10/1998 | Ritchie .................. | 128/201.23 |
| 6,165,197 | A | * | 12/2000 | Yock .......................... | 606/194 |
| 6,328,031 | B1 | * | 12/2001 | Tischer et al. .......... | 128/201.25 |
| 6,370,692 | B1 | * | 4/2002 | Duyn et al. ....................... | 2/86 |
| 6,440,061 | B1 | * | 8/2002 | Wenner et al. .............. | 600/114 |
| 6,460,538 | B1 | * | 10/2002 | Kemp .................... | 128/201.22 |
| 6,477,712 | B1 | * | 11/2002 | Jones .............................. | 2/69 |
| 6,682,519 | B1 | * | 1/2004 | Schon ......................... | 604/508 |
| 6,792,623 | B2 | * | 9/2004 | Luppi ......................... | 2/171.3 |
| 6,854,459 | B1 | * | 2/2005 | Cox ....................... | 128/201.23 |
| 6,957,653 | B2 | * | 10/2005 | Campbell et al. ...... | 128/206.21 |
| 7,104,264 | B2 | * | 9/2006 | Lee et al. ............... | 128/201.22 |
| 2002/0046752 | A1 | * | 4/2002 | Tischer et al. .......... | 128/201.29 |
| 2003/0131846 | A1 | * | 7/2003 | Campbell et al. ...... | 128/201.25 |
| 2003/0135915 | A1 | * | 7/2003 | Luppi ............................ | 2/424 |
| 2005/0015850 | A1 | * | 1/2005 | Waldman ....................... | 2/205 |
| 2005/0060789 | A1 | * | 3/2005 | Waldman ....................... | 2/205 |

* cited by examiner

*Primary Examiner*—Steven O Douglas
(74) *Attorney, Agent, or Firm*—Hedman & Costigan, P.C.; James V. Costigan

(57) ABSTRACT

A helmet for artificial respiration without the aid of tracheal tubes comprises a container body (12), having at least a transparent portion (14) and in which a patient's head can be housed, and a collar for air-tight application to the patient's neck, which consists of at least a rigid ring (15, 15'), equipped with a series of gas administration connection and accessory-holder fittings (17), said rigid ring (15, 15') being the only part of the helmet (10) connected to the outside when operating, wherein an opening (31) is present on the container body (12) for rapid access to the patient, which is substantially hermetically closed by rapid coupling elements (32).

3 Claims, 5 Drawing Sheets

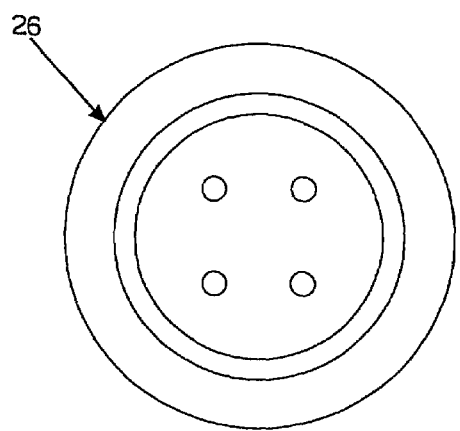
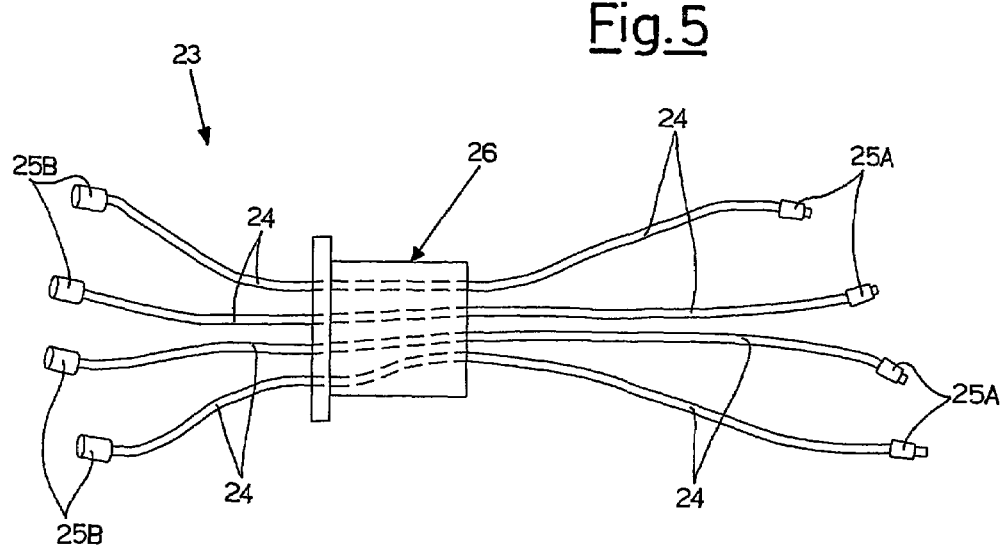

HELMET FOR ARTIFICIAL RESPIRATION

The present invention relates to a helmet for artificial respiration without the aid of a facial mask or tracheal tubes.

In oxygenation and ventilation with continuous positive pressure, so-called CPAP, which is effected, for example, in reanimation, intensive care and pneumology units, in infective departments, in medicine, as well as in hyperbaric chambers, and more recently also in home care, facial masks, tracheal tubes or helmets are currently used, the latter comprising a container body made of a flexible plastic material and equipped with a collar for air-tight application to the patient's head.

In the known helmets, the flexible container body is equipped with an air inlet mouth connected to a ventilation machine and a discharge outlet.

These constitute the so-called CPAP or Non-Invasive Ventilation, NIV, techniques which are particularly useful in many fields of application.

Compared with invasive artificial ventilation, effected through tracheal tubes or tracheotomic cannulas, non-invasive ventilation is, for example, particularly suitable as it is more comfortable for the patient, less traumatic and subject to fewer risks of infection from tracheal intubation, especially for cases in which the treatment is prolonged for long periods of time.

One of the disadvantages of the known helmets for artificial respiration is that they cannot be easily interfaced with a high number of diagnostic machines and devices and for the administration of therapies and connection of various accessories. Some types of cables or tubes, in fact, which must be brought close to the patient's head or neck, such as Central Venous Catheters, must be passed below the air-tight ring of the helmet, which presses on the patient's neck. This not only causes discomfort for the patient but also creates non-optimal sealing conditions of the pressures towards the outside of the helmet.

An object of the present invention is to provide a helmet for artificial respiration which is more comfortable and with an improved air-tightness.

Another object of the present invention is to provide a helmet for artificial respiration suitable for being connected in a versatile way to a high number of machines and/or accessory-devices for therapy or diagnosis.

Yet another object of the present invention is to provide a helmet for artificial respiration which is particularly simple and functional, with limited costs.

These objects according to the present invention are achieved by providing a helmet for artificial respiration as described in claim 1.

Further characteristics are included in the dependent claims.

The characteristics and advantages of a helmet for artificial respiration according to the present invention will appear more evident from the following illustrative but non-limiting description, referring to the schematic drawings enclosed, in which:

FIG. 5 is a side view of an extension element of a central venous catheter specifically produced for the artificial respiration helmet according to the invention;

FIG. 6 shows a detail of the extension element of FIG. 5.

Figure 1:
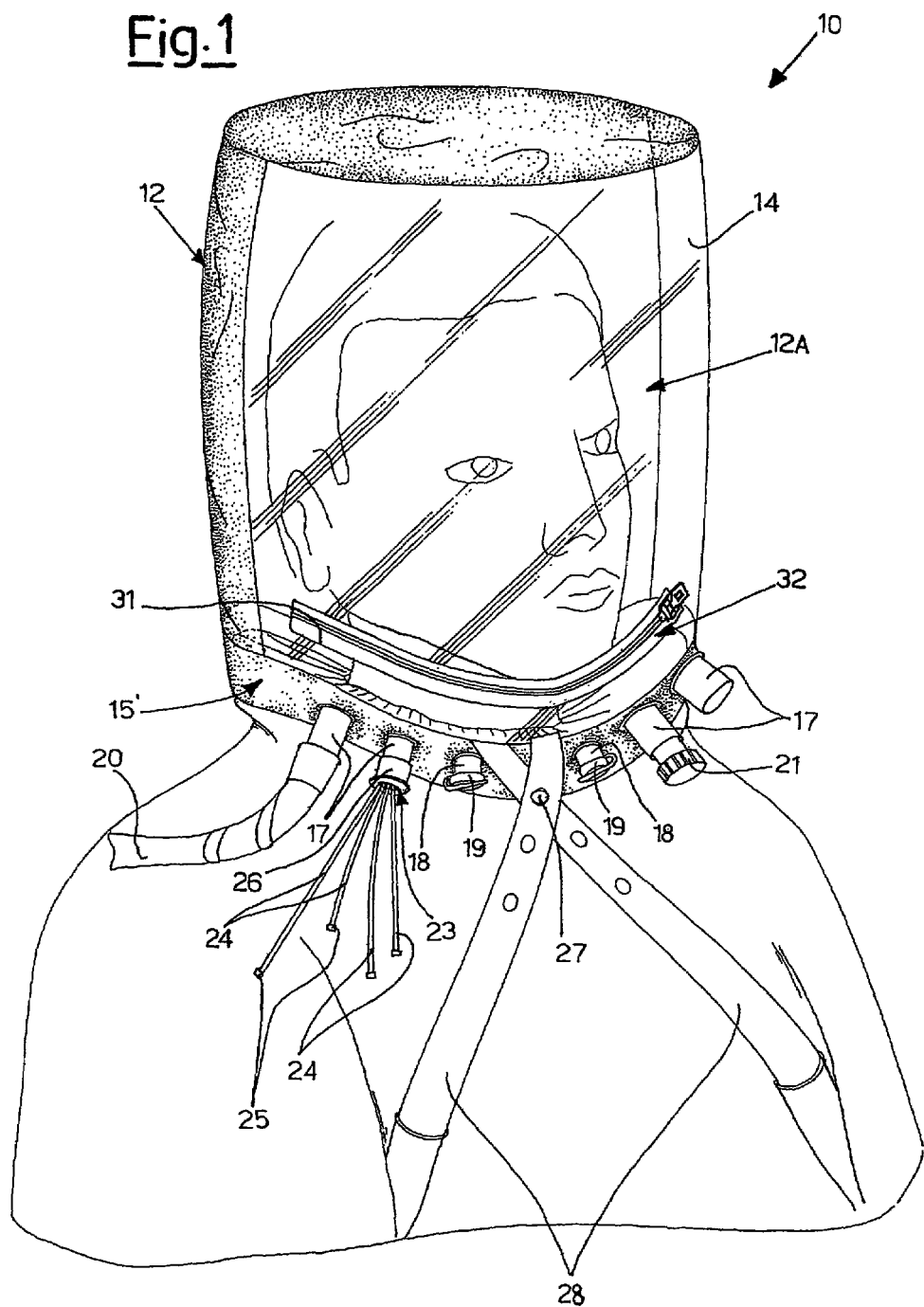
FIG. 1 shows an embodiment of a helmet for artificial respiration according to the present invention, worn by a patient.

With reference to the figures, these illustrate an artificial respiration helmet without the aid of masks or tracheal tubes, indicated as a whole with 10, comprising a container body 12 and a collar for air-tight application to the patient's head.

The container body 12 is made of a flexible plastic material and can, for example, be equipped with a transparent front portion 14, as shown in the figures, which allows the patient wearing the helmet 10 to look outside.

In the lower part, the container body 12 is connected to the collar, comprising a rigid ring 15 and a lower ring 16 made of an elastic plastic material which forms the air-tight seal around the patient's neck.

Figure 2:
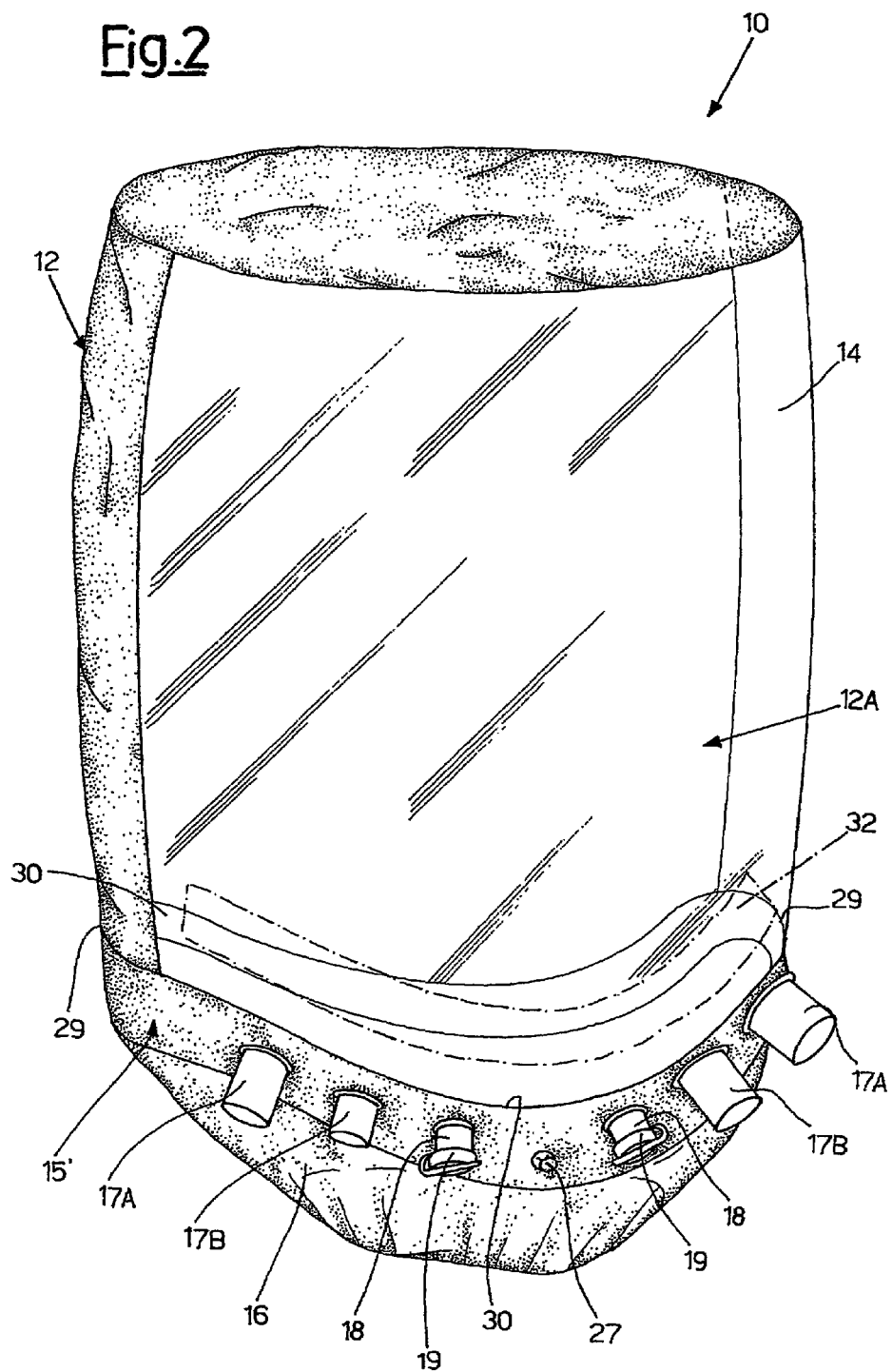
FIG. 2 is a perspective view of the helmet of FIG. 1.
Figure 3:
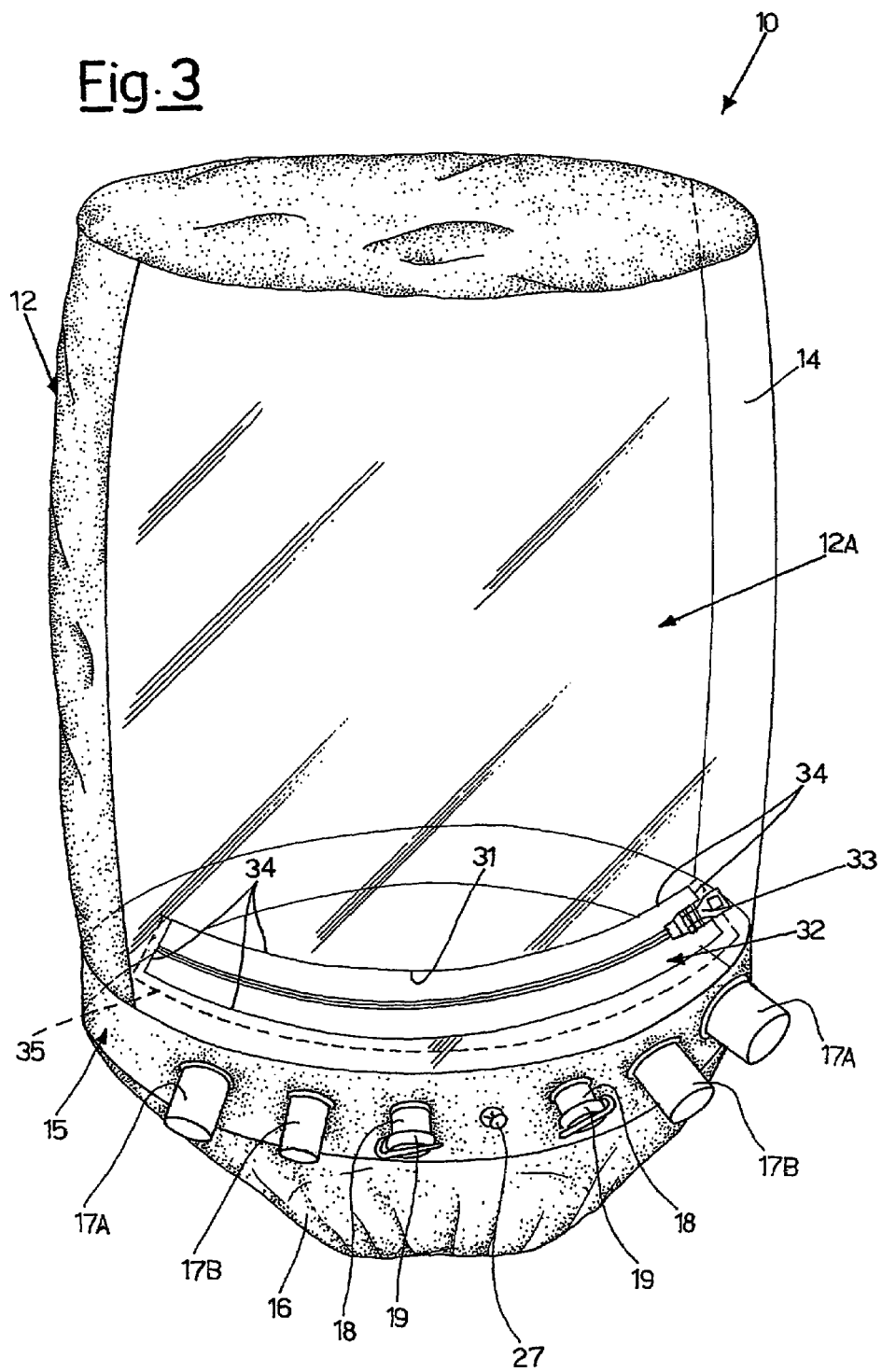
FIG. 3 is a perspective view of a further embodiment of the helmet for artificial respiration, according to the invention.

FIGS. 2 and 3 illustrate two possible embodiments of the artificial respiration helmet 10, object of the present invention. On a front portion 12A of the container body 12, there is an opening 31 for rapid access to the patient, which is substantially hermetically closed by rapid coupling elements 32, such as, for example, a zip made of a plastic material, optionally equipped with a cursor 33.

In particular, in FIG. 2, the arrangement of the rapid coupling elements 32 is indicated with a dash-and-dotted lines.

Figure 4:
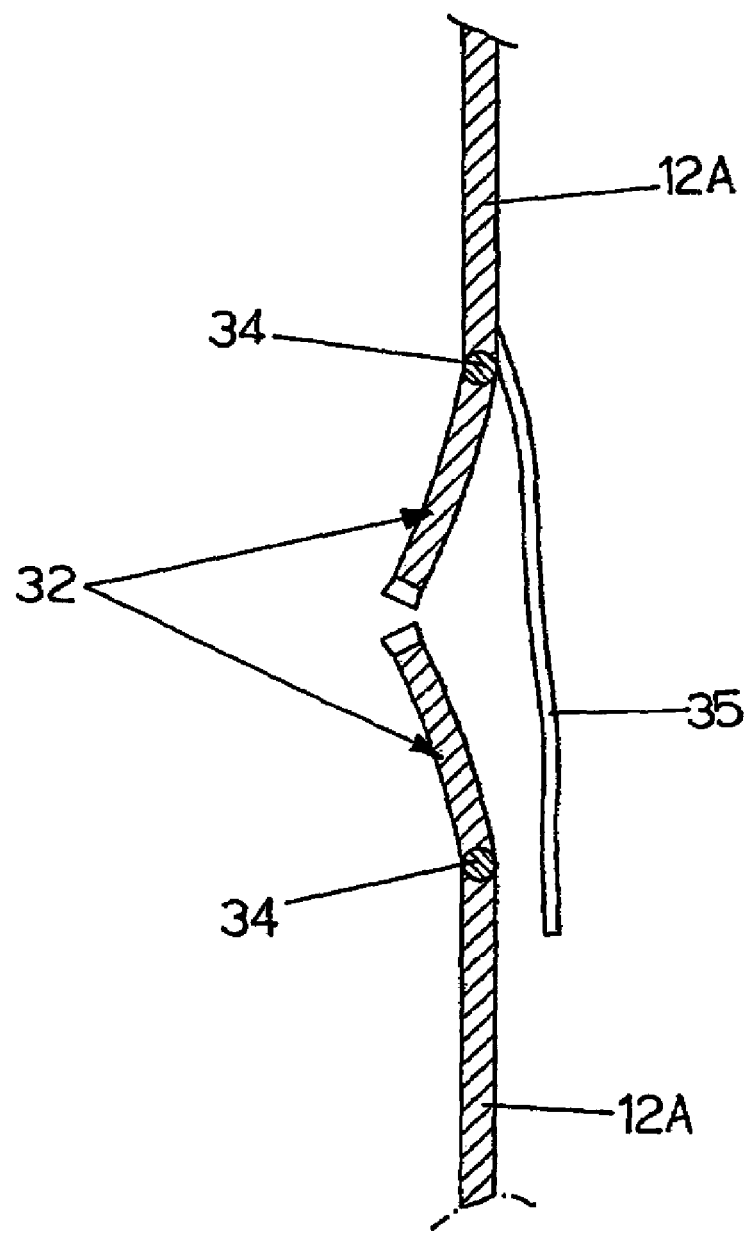
FIG. 4 is a sectional view of an enlarged detail of rapid coupling elements for the closing of an access opening to the patient.

The zip 32, of which FIG. 4 illustrates an enlarged detail in section, is joined to the container body 12 by means of welding edges 34, effected on a perimeter of the opening 31, which form an air-tight connection with respect to the air contained inside the helmet 10.

In addition, in order to reduce to the minimum any possible air leakage through the access opening 31 of the helmet, object of the present invention, the zip (32) is of the air-tight type, i.e. suitable for preventing any passage of air through coupled margins.

As an additional safety element against air leakage from the opening 31, a safety membrane 35, welded along one of its upper edges, for example in correspondence with the welding edges 34 of the zip 32, is applied near said opening 31.

The membrane 35, which in a preferred embodiment shown in detail in FIG. 3, extends for the whole length of the zip 32, due to the pressure present inside the helmet when functioning, is pressed against the zip and guarantees air-tightness.

In FIG. 4, to provide a clearer illustration, the zip 32 is shown in an open position and with the membrane 35 in rest position, not in contact with the zip 32.

A further embodiment, not shown, can comprise the use of several separate safety membranes 35 applied in correspondence with the ends of the zip, which form the areas which are particularly risky with respect to air leakage.

The rapid access opening 31 is preferably horizontal, is situated in a position slightly above the ring 15 or 15' and substantially relates to the whole front portion 12A. In this way, when the rapid coupling elements 32 are open, it is possible to pull the upper part of the helmet 10 backwards like a "hood" to rapidly free the patient's head. It is thus possible to satisfy the patient's requirements, also in any possible emergency situations, without having to remove the whole device and subsequently replace it.

The access opening 31 can also be positioned in different portions of the container body 12 also otherwise oriented. The production of an opening 31 with reduced dimensions would only allow access to the patient, but not the possibility of pulling the container body backwards to free the patient's head.

The artificial respiration helmet, object of the present invention, can also be without an access opening 31, according to a simplified embodiment, not shown.

The rigid ring, which in FIGS. 2 and 3 is shown according to two different embodiments 15 and 15', has a series of gas administration connection and accessory-holder fittings 17, in any number according to the invention.

Furthermore, the rigid ring can have one or more air-tight access elements 18.

The rigid ring 15 or 15' forms the only part of the helmet 10 which can be connected with the outside under operating conditions, thus improving interaction with the ventilation machines and reducing the response times and intervention delays of the apparatuses themselves, normally present when the gas inlet connections are inserted on the soft and flexible body of the helmet.

The air-tight access elements 18, which are equipped, for example, with an internal expansible elastic membrane, not shown, and a safety plug 19, are used for inserting, when necessary, auxiliary means inside the helmet 10, such as probes for feeding the patient or the like.

The accessory-holder fittings 17 are, for example, male 17A or female 17B of the standardized type according to the international ISO regulations. This guarantees the interfaceability with a high number of machines and/or devices and/or accessories for diagnosis or therapy administration.

According to what is schematically illustrated in FIG. 1, the male 17A or female 17B fittings are, for example, suitable for the air-tight connection of tubes 20 or tubular accessory elements 21 for the adduction of gaseous mixtures and discharge of air, they are also suitable for the connection of accessories, such as anti-microbial filters, valves, PEEP valves, overpressure safety valves, "T" connectors and other accessories, not shown. When not used, the fittings 17 are closed by an air-tight plug.

In particular, one of the accessory-holder fittings 17 situated on the rigid ring 15 or 15' can be an extendable fitting specifically produced for a central venous catheter, said catheter normally used for example for patients in reanimation therapy.

An extension element 23 for a central venous catheter or CVC, can in fact be air-tight connected to one of the fittings 17. The element 23 consists of a series of tubes 24, in the example of FIG. 5, four tubes, equipped at both ends with connection devices 25, male 25A and female 25B respectively, for example of the "Luer Lock" type, capable of externally carrying the same number of tubes, not shown, which branch out from the central venous catheter inserted in the patient.

The extension tubes 24 are fixed, for example, immersed in plastic material, or sliding but always air-tight, in a sleeve 26 which acts as an air-tight plug. The sleeve 26, shown in FIG. 6, can be inserted, for example, in the female fitting 17B present on the rigid ring 15 or 15' to the right or to the left, depending on the side of application of the central venous catheter to the patient.

The accessory-holder fittings 17, shown in the figures for illustrative but non-limiting purposes, are symmetrically distributed on the right-hand side and on the left-hand side of the helmet 10 to indifferently allow access to the helmet from both sides, or possibly, contemporaneous access from various sides if a high number of machines or devices must be connected.

Furthermore, a hooking element 27 is present on the rigid ring 15 or 15', for braces 28, of the axillary type, which hold the helmet in position on the patient's head acting against the pressure which tends to lift it.

FIG. 2 illustrates a preferred embodiment of the helmet 10, object of the present invention, in which the rigid ring 15' is anatomically shaped. The rigid ring 15' is, in fact, equipped with two side portions curving upwards 29 diametrically opposed and fitted on the patient's shoulders, as schematically shown in FIG. 1, and also with two portions diametrically opposed curving downwards 30, positioned in front in correspondence with the sternum and behind on the back.

The production of an anatomically shaped rigid ring 15', i.e. shaped so as to obtain a better support on the shoulders, provides greater comfort for the patient.

Furthermore, as the distance between the rigid ring 15' and the patient's body is more or less constant along the whole perimeter, a better seal is obtained on the part of the lower ring 16 of the helmet 10 on the patient's neck, also applying less forces to maintain the helmet in position.

The artificial respiration helmet, object of the present invention, has the advantage of being more practical for use when applied to the patient by specialized staff and consequently more comfortable for the patient himself.

The artificial respiration helmet, object of the present invention, consequently has the advantage of being more comfortable for the patient, as it reduces the pressure of the collar on the shoulders and of not passing tubes or cables between the patient's neck and the lower air-tight ring.

A further advantage with respect to the patient's comfort and also the practicality and good functioning of the machinery used, consists in eliminating the air inlet and outlet mouths from the container body made of a soft and flexible material, which, in the known helmets, cause delays in the response and intervention times of the machinery, such as, for example, a reduction in the so-called "trigger sensitivity" in reanimation ventilators.

In addition, the helmet according to the invention is advantageously designed for being interfaced with a high number of therapy and diagnosis machines and accessories without jeopardizing its air-tight seal towards the outside.

A further advantage of the embodiment of the helmet equipped with an opening for rapid access to the patient is that it facilitates normal cleaning and hygiene operations, for adjusting probes and catheters, and also for allowing the temporary interruption of the therapy without having to remove the whole device from the patient.

Furthermore, above all in the case of emergencies, the operations necessary for removing the helmet can require excessively long times which can endanger the patient's life.

Numerous modifications and variations can be applied to the artificial respiration helmet thus conceived, all included in the scope of the invention; furthermore, all the details can be substituted by technically equivalent elements. In practice, the materials used, as also the dimensions, can vary according to technical demands.

The invention claimed is:

1. A helmet for artificial respiration without the aid of masks or tracheal tubes, said helmet consisting essentially of a container body (12), having at least a transparent portion (14) in which a head of a patient can be housed, and a collar for air-tight application to a patient's neck, said collar consisting essentially of a rigid ring (15, 15') is equipped with a series of gas administration connections and accessory-holder fittings (17) wherein said accessory-holder fittings (17) are male (17A) and female (17B), said series of gas administration connections and accessory-holder fittings (17) being positioned on a surface of said ring (15, 15') surface so as to extend radially from said ring towards the space around the patient with an axis orthogonal to the central axis of the ring, said ring being equipped with a series of air-tight access elements (18) for the insertion of auxiliary means comprising an internal extensible elastic membrane and a safety plug (19), said accessory-holder fittings (17) and said air-tight access elements (18) being all placed only on said rigid ring (15, 15'), said helmet further characterized in that one of said accessory-holder fittings (17) receives a extension element for a central venous catheter, said helmet is further characterized in that said extension element (23) comprises a sleeve (26) and a series of tubes (24), said tubes (24) being fixed with air-tight seal in said sleeve (26) and equipped with connection devices (25) at opposite ends.

2. The helmet according to claim 1, characterized in that said connection devices (25) at opposite ends of said tubes (24), are male (25A) and female (25B) respectively.

3. A helmet for artificial respiration without the aid of masks or tracheal tubes, said helmet consisting essentially of a container body (12), having at least a transparent portion (14) in which a head of a patient can be housed, and a collar for air-light application to a patient's neck, said collar consisting essentially of a rigid ring (15, 15'), characterized in that said rigid ring (15, 15') is equipped with a series of gas administration connections and accessory-holder fittings (17) wherein said accessory-holder fittings (17) are male (17A) and female (17B), said series of gas administration connections and accessory-holder fittings (17) being positioned on a surface of said ring (15, 15') surface so as to extend radially from said ring towards the space around the patient with an axis orthogonal to the central axis of the ring said ring being equipped with a series of air-tight access elements (18) for the insertion of auxiliary means comprising an internal extensible elastic membrane and a safety plug (19), said accessory-holder fittings (17) and said air-tight access elements (18) being all placed only on said rigid ring (15, 15').

\* \* \* \* \*